(12) United States Patent
King et al.

(10) Patent No.: US 8,507,002 B2
(45) Date of Patent: Aug. 13, 2013

(54) HYDROGEL COMPOSITION AND METHODS FOR MAKING THE SAME

(75) Inventors: Richard S. King, Warsaw, IN (US); George Lawrence Grobe, III, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 705 days.

(21) Appl. No.: 12/180,262

(22) Filed: Jul. 25, 2008

(65) Prior Publication Data

US 2008/0292706 A1 Nov. 27, 2008

Related U.S. Application Data

(62) Division of application No. 10/955,463, filed on Sep. 30, 2004, now abandoned.

(51) Int. Cl.
*A61K 9/14* (2006.01)

(52) U.S. Cl.
USPC .......................................................... 424/486

(58) Field of Classification Search
USPC .......................................................... 424/486
See application file for complete search history.

(56) References Cited

U.S. PATENT DOCUMENTS

| | | | |
|---|---|---|---|
| 3,783,872 A | 1/1974 | King | |
| 3,988,274 A * | 10/1976 | Masuhara et al. | 523/106 |
| 4,684,558 A | 8/1987 | Keusch et al. | |
| 4,699,146 A | 10/1987 | Sieverding | |
| 4,734,097 A | 3/1988 | Tanabe et al. | |
| 4,750,482 A | 6/1988 | Sieverding | |
| 4,871,785 A * | 10/1989 | Froix | 523/106 |
| 5,354,835 A | 10/1994 | Blair | |
| 5,674,346 A | 10/1997 | Kindel | |
| 5,681,869 A | 10/1997 | Villain et al. | |
| 5,700,583 A | 12/1997 | Jamiolkowski et al. | |
| 5,733,563 A | 3/1998 | Fortier | |
| 6,184,266 B1 | 2/2001 | Ronan et al. | |
| 6,416,690 B1 | 7/2002 | Soane et al. | |
| 6,471,993 B1 | 10/2002 | Shastri et al. | |
| 6,482,870 B1 | 11/2002 | Hojjati Emami et al. | |
| 6,607,819 B2 | 8/2003 | Wang et al. | |
| 2002/0032297 A1 | 3/2002 | Carlson et al. | |
| 2002/0045706 A1 | 4/2002 | Houston et al. | |
| 2002/0153623 A1 | 10/2002 | Gobron et al. | |
| 2003/0083389 A1 | 5/2003 | Kao et al. | |
| 2003/0083433 A1 | 5/2003 | James et al. | |
| 2004/0091603 A1 | 5/2004 | Priewe | |
| 2006/0074182 A1 | 4/2006 | King et al. | |
| 2006/0083773 A1 | 4/2006 | Myung et al. | |
| 2007/0179605 A1 | 8/2007 | Myung et al. | |

FOREIGN PATENT DOCUMENTS

| | | |
|---|---|---|
| EP | 0651005 A1 | 5/1995 |
| EP | 0661045 B2 | 7/2002 |
| GB | 1395501 A | 5/1975 |
| GB | 2276627 A | 10/1994 |
| JP | 4-268335 A | 9/1992 |
| JP | 6-315526 A | 11/1994 |
| WO | 02/072862 A2 | 9/2002 |
| WO | 02/087645 A1 | 11/2002 |
| WO | 03/071339 A1 | 8/2003 |
| WO | WO 2008/130604 A2 | 10/2008 |

OTHER PUBLICATIONS

Sophia, Susan et al, Grafting of PEO to polymer surfaces using electron beam irradiation, 1997, Department of Chemical Engineering, Massachusetts Institute of Technology, 153-163.*
Doytcheva, M. et al., Ultraviolet0Induced Crosslinking of Solid Poly(ethylene oxide), 1997, John Wiley & Sons, Inc., J Appl Polym Sci, 64, pp. 2299-2307.*
Zainuddin, J. et al, Radiation-induced degradation and crosslinking of poly(ethylene oxide) in solid state, 2002, Journal of Radioanalytical and Nuclear Chemistry, vol. 253, No. 3, pp. 339-344.*
Dow Chemical Co., "POLYOX Water-Soluble Resins: Antioxidant Package for High Temperature Applicants", Form No. 326-00033-1002AMS (Oct. 2002).
Dow Chemical Co., "POLYOX Water-Soluble Resins: POLYOX WSR Solid Dosage Formulation via Melt Extrusion", Form No. 326-00046-0203AMS (Feb. 2003).
Dow Chemical Co., POLYOX Water-Soluble Resins, Form No. 326-00001-0302 AMS (Mar. 2002).
European Patent Office, European Search Report in European Patent Application No. 05255814.5 (Jan. 26, 2006).
Monis "Hydrogel Contact Lenses", in partial fulfillment of course requirement for MatE 115, San Jose State University, Fall 2002.
Tranquilan-Aranilla et al., Radiation Physics and Chemistry, 55, pp. 127-131 (1999).
European Patent Office, Extended European Search Report in European Patent Application No. 05255814.5-2108 (Feb. 2, 2006).
European Patent Office, Extended European Search Report in European Patent Application No. 09153714.2-1219 (Jul. 10, 2009).
Japanese "Notification of Reasons for Refusal" (Translation) regarding Japanese Patent Application No. 2005-285072 dated May 12, 2011 (4 pages).

* cited by examiner

*Primary Examiner* — Daniel Sullivan
*Assistant Examiner* — Trevor Love
(74) *Attorney, Agent, or Firm* — Barnes & Thornburg LLP

(57) ABSTRACT

The invention provides a hydrogel composition comprising water and a hydrophilic polymer, wherein the hydrogel composition has (a) an ultimate tensile strength of about 10 kPa or more, (b) a compressive strength of about 70 kPa or more, or (c) an ultimate tensile strength of about 10 kPa or more and a compressive strength of about 70 kPa or more. The invention further provides methods for producing a hydrogel composition.

14 Claims, No Drawings

HYDROGEL COMPOSITION AND METHODS FOR MAKING THE SAME

CROSS-REFERENCE TO A RELATED APPLICATION

This is a divisional of co-pending U.S. application Ser. No. 10/955,463, filed Sep. 30, 2004, the disclosure of which is incorporated by reference.

FIELD OF THE INVENTION

This invention pertains to a hydrogel composition, as well as methods for making the same.

BACKGROUND OF THE INVENTION

A "gel" can be defined as a colloid which is in a form that is more solid than a sol. A "hydrogel" is a gel in which the liquid or dispersion medium is water. Hydrogels can be formed from virtually any substance that is capable of forming stable colloids with water. For example, silica hydrogels are well known and have been utilized in many applications. Hydrogels also can be formed from polymeric substances, such as hydrophilic monomers or polymers.

One of the most common methods for producing hydrogels from hydrophilic monomers or polymers utilizes an aqueous solution of the hydrophilic monomer or polymer. In particular, the process begins with the preparation of a dilute aqueous solution of the hydrophilic monomer or polymer. The dilute solution is then irradiated or otherwise treated (e.g., with a chemical crosslinking agent) in order to form cross-links between the individual monomer or polymer molecules present in the solution. As more and more crosslinks are formed between the molecules, the hydrophilic monomer or polymer begins to form a network of polymer molecules that grows until the aqueous solution gels. The resulting hydrogel contains a three dimensional matrix of cross-linked polymer molecules in which the water from the aqueous solution is encapsulated.

Hydrogels made by the aforementioned process are used in many applications. However, the limitations inherent in the process impact the properties of the hydrogels, which prevents them from being used in many applications. For example, it is often difficult to produce an initial aqueous solution of the hydrophilic monomer or polymer having a concentration high enough to produce a hydrogel having an extensive matrix of crosslinked polymer molecules and any significant mechanical strength (e.g., compressive strength and/or tensile strength). Indeed, the extent of the polymer network and mechanical properties of the hydrogel can suffer even more when the hydrogel is made from medium to high-molecular weight hydrophilic polymers, which tend to have relatively low water solubilities that prevent the use of aqueous dispersions containing any significant amount of the hydrophilic polymer. The relatively weak mechanical properties exhibited by hydrogels made by this process severely hamper the usefulness of such hydrogels in applications that may subject the hydrogel to even moderate mechanical stresses, such as tensile and/or compressive stresses.

Furthermore, insofar as the process requires a uniform aqueous solution of the hydrophilic monomer or polymer, it is difficult to produce a hydrogel that also contains a water-insoluble material, such as a polymer, uniformly dispersed in the hydrogel. More specifically, it is often difficult to maintain a uniform dispersion of the water-insoluble material in the initial aqueous solution of the hydrophilic monomer or polymer such that the water-insoluble material is uniformly distributed in the hydrogel after the monomer or polymer is crosslinked to produce the hydrogel. Utilizing the aforementioned process, it is also often difficult to control the final water content of the hydrogels produced by the process. In particular, the final water content of hydrogels produced by the aforementioned process is largely determined by the chemical composition of the hydrogel (i.e., the hydrophilic polymer used to make the hydrogel) and the degree to which the hydrophilic polymer molecules are cross-linked. Therefore, the amount of water contained in the hydrogel will be determined, at least in part, by the particular hydrophilic polymer used to make the hydrogel as well as the degree of cross-linking required to produce a hydrogel having the desired characteristics, and not solely by the desired final water content of the hydrogel.

A need therefore remains for hydrogel compositions exhibiting enhanced mechanical properties relative to hydrogel compositions produced by typical methods. A need also remains for methods of making such hydrogel compositions exhibiting enhanced mechanical properties. The invention provides such a hydrogel composition and methods for making the same. These and other advantages of the invention, as well as additional inventive features, will be apparent from the description of the invention provided herein.

BRIEF SUMMARY OF THE INVENTION

The invention provides a hydrogel composition comprising water and a hydrophilic polymer, wherein the hydrogel composition has (a) an ultimate tensile strength of about 10 kPa or more, (b) a compressive strength of about 70 kPa or more, or (c) an ultimate tensile strength of about 10 kPa or more and a compressive strength of about 70 kPa or more.

The invention further provides a method for producing a hydrogel composition, the method comprising the steps of: (a) providing a compression mold having an internal volume, (b) providing a hydrogel precursor comprising a melt-processable, radiation crosslinkable, hydrophilic polymer, (c) filling at least a portion of the internal volume of the compression mold with the precursor, (d) compressing the precursor contained within the compression mold for a time and under conditions sufficient to form a molded body therefrom, (e) irradiating at least a portion of the molded body for a time and under conditions sufficient to crosslink at least a portion of the hydrophilic polymer contained within the molded body, and (f) hydrating the irradiated molded body for a time and under conditions sufficient to form a hydrogel therefrom.

The invention further provides another method for producing a hydrogel composition, the method comprising the steps of: (a) providing a dispersion of a crosslinking agent, (b) providing a hydrogel precursor comprising a melt-processable, hydrophilic polymer, (c) coating at least a portion of the hydrogel precursor with the dispersion, (d) providing a compression mold having an internal volume, (e) filling at least a portion of the internal volume of the compression mold with the coated precursor produced in step (c), (f) compressing the precursor contained within the compression mold for a time and under conditions sufficient to form a molded body therefrom and crosslink at least a portion of the hydrophilic polymer contained within the molded body, and (g) hydrating the molded body for a time and under conditions sufficient to form a hydrogel therefrom.

DETAILED DESCRIPTION OF THE INVENTION

The invention provides a hydrogel composition comprising water and a hydrophilic polymer. The hydrogel composition has (a) an ultimate tensile strength of about 10 kPa or more, (b) a compressive strength of about 70 kPa or more, or (c) an ultimate tensile strength of about 10 kPa or more and a compressive strength of about 70 kPa or more.

The hydrogel composition of the invention comprises water. Preferably, the water is purified in some manner, such as de-ionization or reverse osmosis. The hydrogel composition of the invention can have any suitable water content. Preferably, the hydrogel composition of the invention has a water content of at least about 30% (e.g., at least about 35% or at least about 38%) more preferably at least about 50%, even more preferably at least about 75%, even more preferably at least about 90%, and most preferably about 92% to about 95%, based on the total weight of the hydrogel composition.

The hydrogel composition of the invention comprises a hydrophilic polymer. The hydrophilic polymer can be any suitable hydrophilic polymer, but hydrophilic polymers having a medium to high molecular weight are preferred. In particular, the hydrophilic polymer preferably has an average molecular weight of about 400,000 atomic mass units or more, more preferably about 500,000 atomic mass units or more, and most preferably about 1,000,000 atomic mass units or more (e.g., about 2,000,000 atomic mass units or more, about 3,000,000 atomic mass units or more, about 4,000,000 atomic mass units or more, or even about 7,000,000 atomic mass units or more).

Preferably, the hydrophilic polymer is a melt-processable, hydrophilic polymer, more preferably a melt-processable, radiation crosslinkable, hydrophilic polymer. As utilized herein, the term "melt-processable" refers to a polymer that can be processed in its molten state using processes such as injection molding, extrusion, blow molding, and/or compression molding. Preferably, a melt processable polymer does not exhibit significant oxidative degradation, decomposition, or pyrolysis at the processing temperatures typically used in such molding processes. The term "radiation crosslinkable," as utilized herein, refers to a polymer that forms crosslinks between individual polymer molecules when the polymer is exposed to a suitable amount of radiation, such as gamma, x-ray, or electron beam radiation. A radiation crosslinkable polymer preferably does not exhibit significant degradation or chain scission when the polymer is irradiated. In a preferred embodiment, the hydrophilic polymer is poly(ethylene oxide).

The hydrogel composition of the invention can have an ultimate tensile strength of about 10 kPa or more. As utilized herein, the term "ultimate tensile strength" refers to the maximum resistance to fracture of a material (e.g., the hydrogel composition) under tensile stress. The ultimate tensile strength can be measured in accordance with the procedures outlined in ASTM Standard D638-03 (Type V) and is considered to be within the ranges set forth herein when so determined by any of the procedures in ASTM Standard D638-03 (Type V). In a preferred embodiment, the hydrogel composition of the invention has an ultimate tensile strength of about 20 kPa or more. In a more preferred embodiment, the hydrogel composition of the invention has an ultimate tensile strength of about 30 kPa or more, most preferably about 35 kPa or more (e.g., about 45 kPa or more, or about 50 kPa or more).

The hydrogel composition of the invention can have a compressive strength of about 70 kPa or more. As utilized herein, the term "compressive strength" refers to the maximum resistance to fracture of a material (e.g., the hydrogel composition) under compressive stress. The compressive strength of the hydrogel composition can be measured using any suitable technique. One suitable technique for determining the compressive strength of a hydrogel is the method of C. Tranquilan-Aranilla et al., which is described in the article "Kappa-carrageenan-polyethylene oxide hydrogel blends prepared by gamma irradiation," Radiation Physics and Chemistry 55:127-131 (1999). Preferably, the compressive strength of the hydrogel composition is determined using a modified version of the technique developed by C. Tranquilan-Aranilla et al. in which the sample used for the test is changed to measure approximately 15.9 mm (0.625 inches) in diameter and about 6.4 mm (0.25 inches) in thickness. The crosshead speed used in the modified technique is approximately 10 mm/min (0.4 inches/min), which is the same crosshead speed used by C. Tranquilan-Aranilla et al. The compressive strength of a hydrogel is considered to be within the ranges set forth herein when determined using the aforementioned preferred technique (i.e., the modified technique based upon the method of C. Tranquilan-Aranilla et al.). In a preferred embodiment, the hydrogel composition of the invention has a compressive strength of about 100 kPa or more. In a more preferred embodiment, the hydrogel composition of the invention has a compressive strength of about 200 kPa or more, most preferably about 300 kPa or more (e.g., about 400 kPa or more, about 440 kPa or more, about 500 kPa or more, about 600 kPa or more, or about 620 kPa or more).

The hydrogel composition of the invention has an ultimate tensile strength falling within one of the ranges set forth above, a compressive strength falling within one of the ranges set forth above, or a combination of both an ultimate tensile strength falling within one of the ranges set forth above and a compressive strength falling within one of the ranges set forth above. Preferably, the hydrogel composition of the invention has both an ultimate tensile strength falling within one of the ranges set forth above and a compressive strength falling within one of the ranges set forth above. For example, in a preferred embodiment, the hydrogel composition of the invention has an ultimate tensile strength of about 10 kPa or more and a compressive strength of about 70 kPa or more. In a particularly preferred embodiment, the hydrogel composition of the invention has an ultimate tensile strength of about 35 kPa or more (e.g., about 45 kPa or more, or about 50 kPa or more) and a compressive strength of about 300 kPa or more (e.g., about 400 kPa or more, or about 440 kPa or more).

The hydrogel composition of the invention can further comprise a second polymer in addition to the hydrophilic polymer. The second polymer can be any suitable polymer, such as a hydrophilic polymer or a hydrophobic or water-insoluble polymer. Hydrophilic polymers suitable for use as the second polymer include, but are not limited to, polyethylene glycol, polyethylene glycol copolymers (e.g., poly(ethylene glycol-co-propylene glycol) copolymers, poly(ethylene glycol)-poly(propylene glycol)-poly(ethylene glycol) block copolymers, or poly(propylene glycol)-poly(ethylene glycol)-poly(propylene glycol) block copolymers), poly(propylene glycol), poly(2-hydroxyethyl methacrylate), poly(vinyl alcohol), poly(acrylic acid), poly(methacrylic acid), polyvinylpyrrolidone, cellulose ether, alginate, chitosan, hyaluronate, collagen, and mixtures or combinations thereof. Alternatively, the second polymer can be an absorbable polymer (i.e., a polymer which degrades in vivo into non-toxic substances that can be eliminated by the body). Absorbable polymers suitable for use as the second polymer include, but are not limited to, polylactic acid, polyglycolic acid, polydioxanone, polycaprolactone, beta-hydroxy acid polymers, and combinations thereof.

The hydrogel composition of the invention also can contain any suitable active ingredient, such as a drug (e.g., lidocaine), a therapeutic agent, or a humectant. The active ingredients can be incorporated in the hydrogel composition by any suitable means. For example, the active ingredient can be incorporated (e.g., dry blended) into the precursor utilized to produce the hydrogel composition. Alternatively, the active ingredient can be incorporated into the hydrogel composition during the hydration process. In particular, the hydrogel precursor can be hydrated utilizing an aqueous solution containing the active ingredient. Alternatively, a hydrogel composition according to the invention can be dehydrated or dried to produce a xerogel, and then the xerogel can be hydrated utilizing an aqueous solution containing the active ingredient.

The hydrogel composition of the invention is well suited for many applications, especially those applications requiring hydrogels capable of withstanding moderate to high mechanical stresses without failing. For example, the hydrogel composition of the invention is well suited for use in many biomedical applications. Suitable biomedical applications include, but are not limited to, anti-adhesion barriers (e.g., a barrier that prevents the abnormal adhesion of collagen fibers to structures during immobilization following trauma or surgery), contact lenses, drug delivery devices, prosthetic nuclear discs, wound dressings, and soft tissue repair structures (e.g., artificial cartilage).

The invention also provides methods for producing a hydrogel composition. In a first embodiment, the invention provides a method for producing a hydrogel composition, the method comprising the steps of (a) providing a compression mold having an internal volume, (b) providing a hydrogel precursor comprising a melt-processable, radiation crosslinkable, hydrophilic polymer, (c) filling at least a portion of the internal volume of the compression mold with the precursor, (d) compressing the precursor contained within the compression mold for a time and under conditions sufficient to form a molded body therefrom, (e) irradiating at least a portion of the molded body for a time and under conditions sufficient to crosslink at least a portion of the hydrophilic polymer contained within the molded body, and (f) hydrating the irradiated molded body for a time and under conditions sufficient to form a hydrogel therefrom.

The hydrogel precursor utilized in this first method embodiment of the invention comprises a melt-processable, radiation-crosslinkable, hydrophilic polymer. The melt-processable, radiation-crosslinkable, hydrophilic polymer contained in the hydrogel precursor can be any suitable polymer, but hydrophilic polymers having a medium to high weight average molecular weight are preferred. In particular, the hydrophilic polymer preferably has an average molecular weight of about 400,000 atomic mass units or more, more preferably about 500,000 atomic mass units or more, and most preferably about 1,000,000 atomic mass units or more (e.g., about 2,000,000 atomic mass units or more, about 3,000,000 atomic mass units or more, or even about 4,000,000 atomic mass units or more). In a preferred embodiment, the hydrophilic polymer is poly(ethylene oxide).

The molded body produced during the compression step of this method embodiment of the invention can be irradiated using any suitable method, many of which are known in the art. For example, the molded body can be irradiated by exposing the mass to a suitable amount of gamma, x-ray, or electron beam radiation. Preferably, the molded body is irradiated by exposing it to about 0.5 Mrad to about 50 Mrad (e.g., about 0.5 Mrad to about 10 Mrad, or about 1.5 to about 6 Mrad) of gamma radiation. While the molded body can be exposed to amounts of radiation falling outside of the aforementioned range, such amounts of radiation tend to produce hydrogels with unsatisfactory properties. In particular, radiation doses of less than about 0.5 Mrad generally provide insufficient cross-linking of the hydrophilic polymer to produce an extensive matrix of cross-linked polymer molecules and a coherent hydrogel. Furthermore, while doses of greater than 50 Mrad may be used, the additional improvement in the extent of cross-linking of the hydrophilic polymer that is achieved generally is offset by the degradation of the hydrophilic polymer that can occur with such high doses of radiation.

Preferably, the molded body is irradiated in an inert or reduced-pressure atmosphere. Irradiating the molded body in an inert (i.e., non-oxidizing) or reduced-pressure atmosphere reduces the effects of oxidation and chain scission reactions which can occur during irradiation in an oxidative atmosphere. Typically, the molded body is placed in an oxygen-impermeable package during the irradiation step. Suitable oxygen-impermeable packaging materials include, but are not limited to, aluminum, polyester coated metal foil (e.g., the Mylar® product available from DuPont Teijin Films), poly-ethylene terephthalate, and poly(ethylene vinyl alcohol). In order to further reduce the amount of oxidation which occurs during the irradiation of the molded body, the oxygen-impermeable packaging may be evacuated (e.g., the pressure within the packaging may be reduced below the ambient atmospheric pressure) and/or flushed with an inert gas (e.g., nitrogen, argon, helium, or mixtures thereof) after the molded body has been placed therein.

In a second embodiment, the invention provides a method for producing a hydrogel composition, the method comprising the steps of (a) providing a dispersion of a crosslinking agent, (b) providing a hydrogel precursor comprising a melt-processable, hydrophilic polymer, (c) coating at least a portion of the hydrogel precursor with the dispersion, (d) providing a compression mold having an internal volume, (e) filling at least a portion of the internal volume of the compression mold with the coated precursor produced in step (c), (f) compressing the precursor contained within the compression mold for a time and under conditions sufficient to form a molded body therefrom and crosslink at least a portion of the hydrophilic polymer contained within the molded body, and (g) hydrating the molded body for a time and under conditions sufficient to form a hydrogel therefrom.

The dispersion of the crosslinking agent utilized in this second method embodiment of the invention can contain any suitable crosslinking agent (e.g., a chemical crosslinking agent) dispersed in any suitable medium. Preferably, the crosslinking agent is a peroxide. Preferred peroxide crosslinking agents have a decomposition temperature of about 100° C. to about 125° C., such as benzoyl peroxide. In a preferred embodiment, the medium of the dispersion is an organic solvent, such as ethyl acetate.

The hydrogel precursor utilized in the second method embodiment of the invention comprises a melt-processable, hydrophilic polymer. The melt-processable, hydrophilic polymer contained in the hydrogel precursor can be any suitable polymer, but hydrophilic polymers having a medium to high weight average molecular weight are preferred. In particular, the hydrophilic polymer preferably has an average molecular weight of about 400,000 atomic mass units or more, more preferably about 500,000 atomic mass units or more, and most preferably about 1,000,000 atomic mass units or more (e.g., about 2,000,000 atomic mass units or more, about 3,000,000 atomic mass units or more, or even about 4,000,000 atomic mass units or more). In a preferred embodiment, the hydrophilic polymer is poly(ethylene oxide).

As noted above, the methods of the invention comprise providing a compression mold for the hydrogel composition having an internal volume. The term "compression mold" is utilized herein to refer to a mold typically having two halves which, when joined together, define an internal volume (i.e., mold cavity). The compression mold can be provided in any suitable configuration. Generally, the compression mold is configured such that the internal volume of the compression mold (i.e., the mold cavity) defines a molded body in a substantially complete form (i.e., in substantially the same form as will be used for the hydrogel composition). However, it will be understood that the molded body produced in step (d) of the first method embodiment and step (f) of the second method embodiment also can be subjected to further processing (e.g., machining) to provide the molded body in a form that will produce a hydrogel composition having the desired final form.

The hydrogel precursors utilized in the methods of the invention can be provided in any suitable form. For example, the hydrogel precursor can be provided in the form of a molten matrix containing the hydrophilic polymer and any other suitable additives (e.g., second polymer, active ingredient, etc.). Preferably, the hydrogel precursor is provided in a form selected from the group consisting of a powder, pellets, or a combination thereof.

The hydrogel precursors utilized in the methods of the invention can further comprise a second polymer in addition to the hydrophilic polymer. The second polymer can be any suitable polymer, such as a hydrophilic polymer or a hydrophobic or water-insoluble polymer. Hydrophilic polymers suitable for use as the second polymer include, but are not limited to, polyethylene glycol, polyethylene glycol copolymers (e.g., poly(ethylene glycol-co-propylene glycol) copolymers, poly(ethylene glycol)-poly(propylene glycol)-poly(ethylene glycol) block copolymers, or poly(propylene glycol)-poly(ethylene glycol)-poly(propylene glycol) block copolymers), poly(propylene glycol), poly(2-hydroxyethyl methacrylate), poly(vinyl alcohol), poly(acrylic acid), poly(methacrylic acid), polyvinylpyrrolidone, cellulose ether, alginate, chitosan, hyaluronate, collagen, and mixtures or combinations thereof. Alternatively, the second polymer can be an absorbable polymer (i.e., a polymer which degrades in vivo into non-toxic substances that can be eliminated by the body). Absorbable polymers suitable for use as the second polymer include, but are not limited to, polylactic acid, polyglycolic acid, polydioxanone, polycaprolactone, beta-hydroxy acid polymers, and mixtures or combinations thereof.

When present in the hydrogel precursor, the optional second polymer can be incorporated into the hydrogel precursor by any suitable means. For example, when the optional second polymer is melt-processable, the second polymer can be melted and uniformly dispersed in a molten matrix of the hydrophilic polymer. When the optional second polymer is not melt-processable, the second polymer can be dry blended with the hydrophilic polymer to produce a polymer blend or mixture prior to the compression molding step.

The hydrogel precursors utilized in the methods of the invention can also contain any suitable active ingredient, such as a drug (e.g., lidocaine), therapeutic agent, or humectant. The active ingredients can be incorporated in the hydrogel precursor by any suitable means. For example, the active ingredient can be incorporated (e.g., dry blended) into the precursor utilized to produce the hydrogel composition. Alternatively, the hydrogel precursor can be coated with the active ingredient, for example, by immersing at least a portion of the hydrogel precursor in a solution or dispersion containing the active ingredient and subsequently drying the coated precursor to remove the liquid medium.

As noted above, at least a portion of the internal volume of the compression mold (i.e., mold cavity) is filled with the hydrogel precursor. Preferably, the portion of the internal volume of the compression mold filled with the mixture comprises a portion of a surface layer of the final hydrogel composition. More preferably, substantially all of the internal volume of the compression mold is filled with the hydrogel precursor. When only a portion of the internal volume of the compression mold is filled with the hydrogel precursor, the remaining portion of the internal volume of the compression mold preferably is filled with another melt-processable polymer, such as ultrahigh molecular weight polyethylene.

After at least a portion of the internal volume of the compression mold is filled, the hydrogel precursor contained within the compression mold is compressed for a time and under conditions (e.g., pressure and temperature) sufficient to form a molded body therefrom. It will be understood that the hydrogel precursor is compressed by any suitable means, such as by mating the two halves of a two-part compression mold and applying an external force in a direction such that any substance contained within the mold (e.g., the hydrogel precursor) is subjected to a compressive force.

Typically, the precursor is subjected to a pressure of about 3,400 kPa to about 28,000 kPa during the compression molding step. Preferably, the precursor is subjected to a pressure of about 3,800 kPa to about 14,000 kPa. During the compression molding step, the precursor typically is subjected to a temperature of about 70° C. to about 200° C. Preferably, the precursor is subjected to a temperature of about 90° C. to about 180° C., more preferably a temperature of about 120° C. to about 140° C., during the compression molding step. The hydrogel precursor can be compressed in the compression mold for any amount of time sufficient to form a molded body therefrom. Typically, the precursor is compressed for about 5 to about 30 minutes, more preferably about 5 to about 10 minutes, during the compression molding step. It will also be understood that the particular time and conditions (e.g., pressure and temperature) necessary to form a molded body from the hydrogel precursor will depend upon several factors, such as the composition of the hydrogel precursor (e.g., the type and/or amount of melt-processable, hydrophilic polymer contained in the precursor), and the size (e.g., thickness) of the desired molded body, as well as other factors.

The molded body produced during the inventive methods can be hydrated to form the hydrogel composition using any suitable technique. Typically, at least a portion of the molded body is submerged in an aqueous solution (e.g., de-ionized water, water filtered via reverse osmosis, a saline solution, or an aqueous solution containing a suitable active ingredient) for an amount of time sufficient to produce a hydrogel composition having the desired water content. For example, when a hydrogel composition comprising the maximum water content is desired, the molded body is submerged in the aqueous solution for an amount of time sufficient to allow the molded body to swell to its maximum size or volume. Typically, the molded body is submerged in the aqueous solution for at least about 50 hours, preferably at least about 100 hours, and more preferably about 120 hours to about 240 hours (e.g., about 120 hours to about 220 hours). It will be understood that the amount of time necessary to hydrate the molded body to the desired level to form the hydrogel composition will depend upon several factors, such as the composition of the hydrogel precursor (e.g., the type and/or amount of melt-processable, hydrophilic polymer contained in the precursor), the size (e.g., thickness) of the molded body, and the temperature of the aqueous solution, as well as other factors. The aqueous solution used to hydrate the molded body can be maintained at any suitable temperature. Typically, the aqueous solution is maintained at a temperature of at least about 25° C., more preferably at a temperature of about 30° C. to about 100° C., and most preferably at a temperature of about 40° C. to about 90° C. (e.g., about 50° C. to about 90° C., or about 50° C. to about 80° C.).

The methods of the invention can further comprise the step of sterilizing the hydrogel composition using any suitable process. The hydrogel composition can be sterilized at any suitable point, but preferably is sterilized after the molded body/hydrogel precursor is hydrated. Suitable non-irradiative sterilization techniques include, but are not limited to, gas plasma or ethylene oxide methods known in the art. For example, the hydrogel composition can be sterilized using a PlazLyte® Sterilization System (Abtox, Inc., Mundelein, Ill.) or in accordance with the gas plasma sterilization processes described in U.S. Pat. Nos. 5,413,760 and 5,603,895. In some circumstances, such as when the interior portions of the hydrogel composition require sterilization, the hydrogel composition can be sterilized using gamma irradiation at a relatively low dose of approximately 1.5 Mrad to about 4 Mrad using methods known in the art.

The hydrogel compositions produced by the methods of the invention can be packaged in any suitable packaging material. Desirably, the packaging material maintains the sterility of the hydrogel composition until the packaging material is breached.

EXAMPLE

This example further illustrates the invention but, of course, should not be construed as in any way limiting its scope. This example demonstrates the production of a hydrogel composition according to the invention.

A hydrogel precursor comprising poly(ethylene oxide) having an average molecular weight of approximately 7 million atomic mass units (POLYOX™ WSR-303 poly(ethylene oxide) (available from The Dow Chemical Company, Midland, Mich.)) was placed into a compression mold having an internal volume. The internal volume of the compression mold defined a disk measuring approximately 89 mm (3.5 inches) in diameter and approximately 3.2 mm (0.125 inches) in thickness, and the hydrogel precursor completely filled the compression mold. The precursor was packed into the compression mold by subjecting the precursor to a compressive force of approximately 2700 kPa (400 psi) for approximately 2-3 minutes at room temperature. Following the packing step, the temperature within the compression mold was increased from room temperature to approximately 127° C. (260° F.) at a rate of approximately 3.3° C./min (6° F./min) while the pressure on the compression mold was increased from 2700 kPa (400 psi) to about 11,000 kPa (1600 psi). The temperature and pressure within the compression mold were then maintained at approximately 127° C. (260° F.) and 11,000 kPa (1600 psi) for approximately 15 minutes. Following the compression step, the resulting molded disk was cooled from 127° C. (260° F.) to room temperature (i.e., approximately 22° C. (72° F.)) at rate of approximately 3.9° C./min (7° F./min) while the pressure was reduced from 11,000 kPa (1600 psi) to approximately 480 kPa (70 psi). The above-described process was repeated four times to produce a total of five molded disks. Each of the disks was then analyzed to determine the average mechanical properties of a disk produced by the process. The resulting molded disks exhibited an average ultimate tensile strength of approximately 27,650 kPa (4,010 psi), an average elongation at fracture of approximately 800%, and an average Young's modulus of approximately 122 MPa (17,700 psi), as determined in accordance with ASTM Standard D638-03 (Type V).

Five molded disks produced by the above-described process were separately vacuum-packaged in aluminum foil bags. The packaged disks were then irradiated by exposing the disks to approximately 5 Mrad (50 kGy) of gamma radiation. Following the irradiation step, the irradiated disks were maintained in the aluminum foil bags in order to protect the poly(ethylene oxide) contained in the disks from oxidative degradation. Next, the irradiated disks were removed from the foil bag and submerged in water filtered via reverse osmosis. The molded disks were allowed to remain in the water, which was maintained at room temperature (i.e., approximately 22° C. (72° F.)), and swell until an equilibrium state was reached, which typically took approximately 170 hours (7 days). The resulting hydrogel compositions had an average gel content of approximately 74% and an average water content of approximately 92%.

The resulting hydrogel compositions exhibited improved tensile strength when compared to a hydrogel produced by a typical solution-based process. In particular, a hydrogel produced by a typical solution-based process exhibited an ultimate tensile strength that was too low to be measured in accordance with the procedures set forth in ASTM Standard D638-03 (Type V). Indeed, the hydrogel sample used in taking the measurements typically fractured before the sample could be mounted on the testing apparatus. Conversely, the hydrogel compositions of the invention exhibited an average ultimate tensile strength of approximately 52 kPa (7.6 psi) and an average elongation at fracture of approximately 253%, as determined in accordance with ASTM Standard D638-03 (Type V).

The resulting hydrogel compositions also exhibited improved compressive strength when compared to hydrogels produced by the solution-based process. A hydrogel produced by a typical solution-based process exhibited a maximum compressive strength of approximately 41 kPa (6 psi), as determined using the preferred modified technique of C. Tranquilan-Aranilla et al. described above. By way of contrast, the hydrogel compositions of the invention exhibited an average compressive strength of approximately 630 kPa (92 psi), when measured using the same procedure. The hydrogel compositions of the invention also exhibited an elasticity sufficient to allow the hydrogel composition to retain its original shape after it has been compressed to a height equal to approximately 50% of its original (i.e., uncompressed) height.

As evidenced by the data set forth above, the hydrogel composition of the invention exhibits improved mechanical properties as compared to hydrogels produced by typical processes, such as a solution-based process. In particular, the tensile properties of the hydrogel composition of the invention are significantly improved over typical hydrogels. Also, the compressive strength of the hydrogel composition of the invention is over ten times greater than the compressive strength of typical hydrogels (i.e., hydrogels produced by a typical solution-based process). These improved mechanical properties make the hydrogel composition of the invention suitable for applications in which the hydrogel composition may be subjected to moderate mechanical stresses, such as tensile and/or compressive stresses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for producing a hydrogel composition comprising water and a crosslinked hydrophilic polymer, wherein the hydrogel composition has (a) an ultimate tensile strength of about 10 kPa or more, (b) a compressive strength of about 70 kPa or more, or (c) an ultimate tensile strength of about 10 kPa or more and a compressive strength of about 70 kPa or more, the method comprising the steps of:
   (a) providing a compression mold having an internal volume,
   (b) providing a hydrogel precursor in powder or pellet form comprising a melt-processable, radiation crosslinkable, hydrophilic polymer which is poly(ethyleneoxide) having an average molecular weight of about 1,000,000 atomic mass units or greater,
   (c) filling at least a portion of the internal volume of the compression mold with the precursor,
   (d) compressing the precursor contained within the compression mold to form a molded body therefrom,
   (e) irradiating at least a portion of the molded body by exposing the molded body to gamma, X-ray, or electron beam radiation the absence of water, to crosslink at least a portion of the hydrophilic polymer contained within the molded body, and
   (f) hydrating the irradiated molded body to form a hydrogel composition therefrom;
   wherein the hydrogel composition has a water content of at least 75% by weight,
   wherein the molded body is hydrated by submerging at least a portion of the molded body in an aqueous solution having a temperature of about 50° C. to about 90° C. for about 120 hours to about 220 hours.

2. The method of claim 1, wherein the aqueous solution further comprises an active ingredient selected from the group consisting of a drug, a therapeutic agent, a humectant, and mixtures thereof.

3. A method for producing a hydrogel composition comprising water and a crosslinked hydrophilic polymer, wherein the hydrogel composition has (a) an ultimate tensile strength of about 10 kPa or more, (b) a compressive strength of about 70 kPa or more, or (c) an ultimate tensile strength of about 10 kPa or more and a compressive strength of about 70 kPa or more, the method comprising the steps of:
   (a) providing a dispersion comprising a peroxide crosslinking agent,
   (b) providing a hydrogel precursor in powder or pellet form comprising a melt-processable, hydrophilic polymer which is poly(ethyleneoxide) having an average molecular weight of about 1,000,000 atomic mass units or greater,
   (c) coating at least a portion of the hydrogel precursor with the dispersion,
   (d) providing a compression mold having an internal volume,
   (e) filling at least a portion of the internal volume of the compression mold with the coated precursor produced in step (c),
   (f) compressing the precursor contained within the compression mold to form a molded body therefrom and crosslink in the absence of water at least a portion of the hydrophilic polymer contained within the molded body, and
   (g) hydrating the molded body to form a hydrogel composition therefrom; wherein the hydrogel composition has a water content of at least 75% by weight.

4. The method of claim 3, wherein the peroxide crosslinking agent is benzoyl peroxide.

5. The method of claim 3, wherein the precursor is compressed at a pressure of about 3,800 kPa to about 14,000 kPa during step (f).

6. The method of claim 3, wherein the precursor is heated to a temperature of about 120° C. to about 140° C. during step (f).

7. The method of claim 3, wherein the precursor is compressed for about 5 to about 10 minutes during step (f).

8. The method of claim 3, wherein the molded body is hydrated by submerging at least a portion of the molded body in an aqueous solution having a temperature of about 50° C. to about 90° C. for about 120 hours to about 220 hours.

9. The method of claim 8, wherein the aqueous solution further comprises an active ingredient selected from the group consisting of a drug, a therapeutic agent, a humectant, and mixtures thereof.

10. The method of claim 3, wherein the hydrogel precursor further comprises an active ingredient selected from the group consisting of a drug, a therapeutic agent, a humectant, and mixtures thereof.

11. A method for producing a hydrogel composition comprising water and a crosslinked hydrophilic polymer, wherein the hydrogel composition has (a) an ultimate tensile strength of about 10 kPa or more, (b) a compressive strength of about 70 kPa or more, or (c) an ultimate tensile strength of about 10 kPa or more and a compressive strength of about 70 kPa or more, the method comprising the steps of:
   (a) providing a compression mold having an internal volume,
   (b) providing a hydrogel precursor in powder or pellet form comprising a melt-processable, radiation crosslinkable, hydrophilic polymer which is poly(ethyleneoxide) having an average molecular weight of about 1,000,000 atomic mass units or greater,
(c) filling at least a portion of the internal volume of the compression mold with the precursor,
(d) compressing the precursor contained within the compression mold to form a molded body therefrom,
(e) irradiating at least a portion of the molded body by exposing the molded body to gamma, X-ray, or electron beam radiation the absence of water, to crosslink at least a portion of the hydrophilic polymer contained within the molded body, and
(f) hydrating the irradiated molded body to form a hydrogel composition therefrom;
wherein the hydrogel composition has a water content of at least 75% by weight,
wherein the hydrogel precursor further comprises a second polymer.

12. A method for producing a hydrogel composition comprising water and a crosslinked hydrophilic polymer, wherein the hydrogel composition has (a) an ultimate tensile strength of about 10 kPa or more, (b) a compressive strength of about 70 kPa or more, or (c) an ultimate tensile strength of about 10 kPa or more and a compressive strength of about 70 kPa or more, the method comprising the steps of:
(a) providing a compression mold having an internal volume,
(b) providing a hydrogel precursor in powder or pellet form comprising a melt-processable, radiation crosslinkable, hydrophilic polymer which is poly(ethyleneoxide) having an average molecular weight of about 1,000,000 atomic mass units or greater,
(c) filling at least a portion of the internal volume of the compression mold with the precursor,
(d) compressing the precursor contained within the compression mold to form a molded body therefrom,
(e) irradiating at least a portion of the molded body by exposing the molded body to gamma, X-ray, or electron beam radiation the absence of water, to crosslink at least a portion of the hydrophilic polymer contained within the molded body,
(f) hydrating the irradiated molded body to form a hydrogel composition therefrom, and
(g) incorporating a second polymer into the hydrogel composition;
wherein the hydrogel composition has a water content of at least 75% by weight.

13. The method of claim 3, wherein the hydrogel precursor further comprises a second polymer.

14. The method of claim 3, which further includes incorporating a second polymer into the hydrogel.

* * * * *